(12) United States Patent
Mitelberg et al.

(10) Patent No.: US 8,062,325 B2
(45) Date of Patent: Nov. 22, 2011

(54) IMPLANTABLE MEDICAL DEVICE DETACHMENT SYSTEM AND METHODS OF USING THE SAME

(75) Inventors: Vladimir Mitelberg, Austin, TX (US); John H. Thinnes, Jr., Miami, FL (US); Keith Balgobin, Pembroke Pines, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 1514 days.

(21) Appl. No.: 11/461,245

(22) Filed: Jul. 31, 2006

(65) Prior Publication Data
US 2008/0097462 A1    Apr. 24, 2008

(51) Int. Cl.
*A61M 29/00* (2006.01)
(52) U.S. Cl. .................................................. 606/200
(58) Field of Classification Search ............. 606/108, 606/200
See application file for complete search history.

(56) References Cited

U.S. PATENT DOCUMENTS

| | | |
|---|---|---|
| 1,294,284 A | 2/1919 | Logeman |
| 2,549,731 A | 4/1951 | Wattley |
| 2,638,365 A | 5/1953 | Jones |
| 3,429,408 A | 2/1969 | Maker |
| 3,547,103 A | 12/1970 | Cook |
| 3,963,322 A | 6/1976 | Gryctko |
| 4,655,219 A | 4/1987 | Petruzzi |
| 4,830,002 A | 5/1989 | Semm |
| 5,108,407 A | 4/1992 | Geremia et al. |
| 5,117,838 A | 6/1992 | Palmer et al. |
| 5,122,136 A | 6/1992 | Gugliemi et al. |
| 5,156,430 A * | 10/1992 | Mori ........................ 294/82.23 |
| 5,217,438 A | 6/1993 | Davis et al. |
| 5,217,484 A | 6/1993 | Marks |
| 5,234,437 A | 8/1993 | Sepetka |
| 5,250,071 A | 10/1993 | Palermo |
| 5,261,916 A | 11/1993 | Engelson |
| 5,263,964 A | 11/1993 | Purdy |
| 5,304,195 A | 4/1994 | Twyford et al. |
| 5,334,210 A | 8/1994 | Gianturco |
| 5,350,397 A | 9/1994 | Palermo et al. |
| 5,354,295 A | 10/1994 | Guglielmi et al. |
| 5,382,259 A | 1/1995 | Phelps et al. |
| 5,397,304 A | 3/1995 | Truckai |
| 5,427,118 A | 6/1995 | Nita et al. |
| 5,540,680 A | 7/1996 | Guglielmi et al. |
| 5,571,089 A | 11/1996 | Crocker |
| 5,582,619 A | 12/1996 | Ken |
| 5,601,600 A | 2/1997 | Ton et al. |
| 5,624,449 A | 4/1997 | Pham et al. |

(Continued)

FOREIGN PATENT DOCUMENTS

EP    832607 A1    4/1998

(Continued)

*Primary Examiner* — Gary Jackson
*Assistant Examiner* — Eric Blatt
(74) *Attorney, Agent, or Firm* — Cook Alex Ltd.

(57) ABSTRACT

An implantable medical device detachment system is provided with a carrier member having a compressible portion at a distal end thereof. The compressible portion is moved to a compressed condition to allow an engagement member of the system to releasably engage an implantable device, such as an embolic coil. The carrier member and associated implantable device are fed through a body vessel to a target location, where the device is disengaged from the engagement member. The compressible portion then moves from the compressed condition to an elongated condition to completely separate the implantable device from the engagement member.

11 Claims, 3 Drawing Sheets

U.S. PATENT DOCUMENTS

| | | |
|---|---|---|
| 5,725,546 A | 3/1998 | Samson |
| 5,725,549 A | 3/1998 | Lam |
| 5,746,769 A | 5/1998 | Ton et al. |
| 5,749,894 A | 5/1998 | Engelson |
| 5,765,449 A | 6/1998 | LeMire |
| 5,782,747 A | 7/1998 | Zimmon |
| 5,800,455 A | 9/1998 | Palermo et al. |
| 5,853,418 A | 12/1998 | Ken et al. |
| 5,895,391 A | 4/1999 | Farnholtz |
| 5,895,411 A | 4/1999 | Irie |
| 5,910,144 A | 6/1999 | Hayashi |
| 5,925,059 A | 7/1999 | Palermo et al. |
| 5,989,242 A | 11/1999 | Saadat et al. |
| 6,107,004 A | 8/2000 | Donadio, III |
| 6,113,622 A | 9/2000 | Hieshima |
| 6,190,373 B1 | 2/2001 | Palermo et al. |
| 6,193,728 B1 | 2/2001 | Ken et al. |
| RE37,117 E | 3/2001 | Palermo |
| 6,203,547 B1 | 3/2001 | Nguyen et al. |
| 6,217,566 B1 | 4/2001 | Ju et al. |
| 6,238,415 B1 | 5/2001 | Sepetka et al. |
| 6,277,125 B1 | 8/2001 | Barry et al. |
| 6,280,464 B1 | 8/2001 | Hayashi |
| 6,296,622 B1 | 10/2001 | Kurz et al. |
| 6,338,736 B1 | 1/2002 | Boosfeld et al. |
| 6,346,091 B1 | 2/2002 | Jacobsen et al. |
| 6,361,547 B1 | 3/2002 | Hieshima |
| 6,451,026 B1 | 9/2002 | Biagtan et al. |
| 6,478,773 B1 | 11/2002 | Gandhi et al. |
| 6,500,149 B2 | 12/2002 | Gandhi et al. |
| 6,537,314 B2 | 3/2003 | Langberg et al. |
| 6,544,225 B1 | 4/2003 | Lulo et al. |
| 6,554,849 B1 | 4/2003 | Jones et al. |
| 6,561,988 B1 | 5/2003 | Turturro et al. |
| 6,562,064 B1 | 5/2003 | deBeer |
| 6,585,718 B2 | 7/2003 | Hayzelden et al. |
| 6,607,538 B1 | 8/2003 | Ferrera et al. |
| 6,638,293 B1 | 10/2003 | Makower et al. |
| 6,660,020 B2 | 12/2003 | Wallace et al. |
| 6,685,653 B2 | 2/2004 | Ehr et al. |
| 6,689,141 B2 | 2/2004 | Ferrera et al. |
| 6,749,560 B1 | 6/2004 | Konstorum et al. |
| 6,761,733 B2 | 7/2004 | Chobotov et al. |
| 6,793,673 B2 | 9/2004 | Kowalsky et al. |
| 6,797,001 B2 | 9/2004 | Mathis et al. |
| 6,811,561 B2 | 11/2004 | Diaz et al. |
| 6,835,185 B2 | 12/2004 | Ramzipoor |
| 6,849,081 B2 | 2/2005 | Sepetka et al. |
| 6,849,303 B2 | 2/2005 | Dave |
| 6,902,572 B2 | 6/2005 | Beulke |
| 6,911,016 B2 | 6/2005 | Balzum et al. |
| 6,953,472 B2 | 10/2005 | Palmer et al. |
| 6,958,068 B2 | 10/2005 | Hieshima |
| 6,966,914 B2 | 11/2005 | Abe |
| 6,994,711 B2 | 2/2006 | Hieshima et al. |
| 7,033,374 B2 | 4/2006 | Schaefer et al. |
| 7,044,134 B2 | 5/2006 | Khairkhahan et al. |
| 7,201,768 B2 | 4/2007 | Diaz et al. |
| 7,323,000 B2 | 1/2008 | Monstdt et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg |
| 7,473,266 B2 | 1/2009 | Glaser |
| 7,582,101 B2 | 9/2009 | Jones et al. |
| 7,708,754 B2 | 5/2010 | Balgobin et al. |
| 7,708,755 B2 | 5/2010 | Davis, III et al. |
| 7,722,636 B2 | 5/2010 | Farnan |
| 2001/0002438 A1 | 5/2001 | Sepetka et al. |
| 2001/0044633 A1 | 11/2001 | Klint |
| 2002/0022837 A1 | 2/2002 | Mazzocchi et al. |
| 2002/0082499 A1 | 6/2002 | Jacobsen et al. |
| 2002/0099408 A1 | 7/2002 | Marks et al. |
| 2002/0111647 A1 | 8/2002 | Khairkhahan et al. |
| 2002/0151915 A1 | 10/2002 | Hieshima et al. |
| 2002/0165569 A1 | 11/2002 | Ramzipoor et al. |
| 2003/0125709 A1 | 7/2003 | Eidenschink |
| 2003/0220666 A1 | 11/2003 | Mirigian |
| 2004/0006363 A1 | 1/2004 | Schaefer |
| 2004/0034363 A1 | 2/2004 | Wilson et al. |
| 2004/0044361 A1 | 3/2004 | Frazier et al. |
| 2004/0073230 A1 | 4/2004 | Mulholland et al. |
| 2004/0111095 A1 | 6/2004 | Gordon et al. |
| 2004/0127918 A1 | 7/2004 | Nikolochyev et al. |
| 2005/0038470 A1 | 2/2005 | van der Burg et al. |
| 2005/0043755 A1 | 2/2005 | Wilson et al. |
| 2005/0113863 A1 | 5/2005 | Ramzipoor et al. |
| 2005/0113864 A1 | 5/2005 | Gandhi et al. |
| 2005/0171572 A1 | 8/2005 | Martinez |
| 2005/0177132 A1 | 8/2005 | Lentz et al. |
| 2005/0216018 A1 | 9/2005 | Sennett |
| 2006/0004346 A1 | 1/2006 | Begg |
| 2006/0100687 A1 | 5/2006 | Fahey et al. |
| 2006/0116714 A1 | 6/2006 | Sepetka et al. |
| 2006/0121218 A1 | 6/2006 | Obara et al. |
| 2006/0189896 A1 | 8/2006 | Davis et al. |
| 2006/0200047 A1 | 9/2006 | Galdonik et al. |
| 2006/0276823 A1 | 12/2006 | Mitelberg et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276828 A1 * | 12/2006 | Balgobin et al. ............... 606/200 |
| 2006/0276829 A1 | 12/2006 | Balgobin et al. |
| 2006/0276830 A1 | 12/2006 | Balgobin et al. |
| 2006/0276832 A1 | 12/2006 | Balgobin et al. |
| 2006/0276833 A1 * | 12/2006 | Balgobin et al. ............... 606/200 |
| 2006/0276834 A1 | 12/2006 | Balgobin et al. |
| 2007/0010849 A1 | 1/2007 | Balgobin et al. |
| 2007/0010850 A1 | 1/2007 | Balgobin et al. |
| 2007/0118172 A1 | 5/2007 | Balgobin |
| 2007/0203519 A1 | 8/2007 | Lorenzo et al. |
| 2007/0239191 A1 | 10/2007 | Ramzipoor |
| 2007/0299422 A1 | 12/2007 | Inganas et al. |

FOREIGN PATENT DOCUMENTS

| | | |
|---|---|---|
| EP | 832607 B1 | 8/2000 |
| EP | 754435 B1 | 12/2003 |
| EP | 1 537 838 A | 6/2005 |
| WO | WO/96/38092 | 12/1996 |
| WO | WO 2004/008974 | 1/2004 |

* cited by examiner

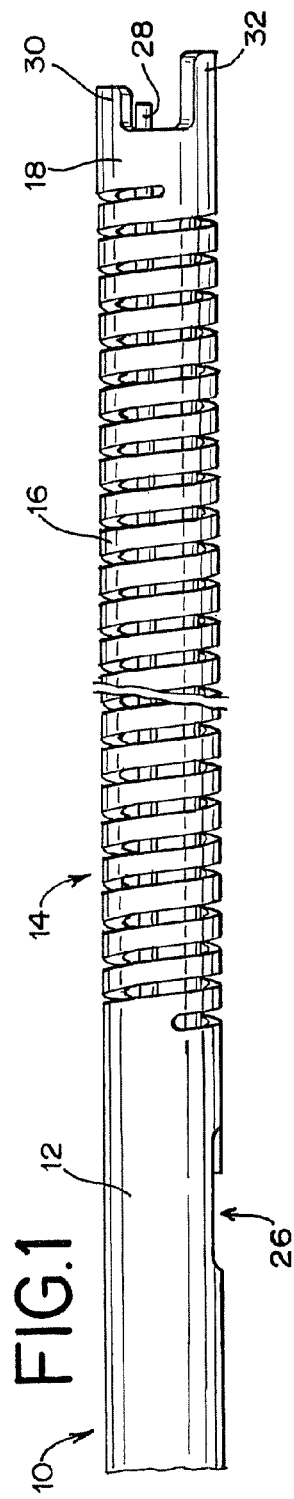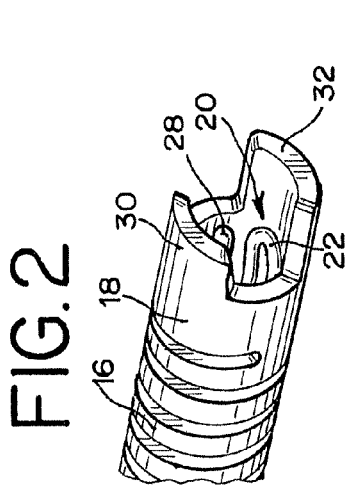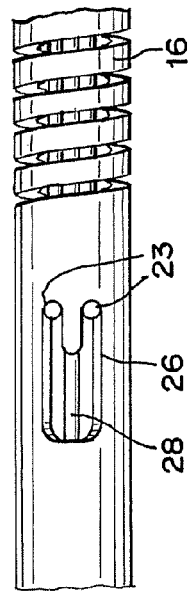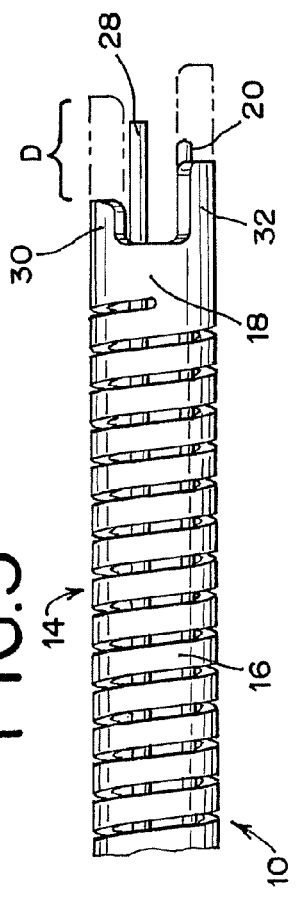

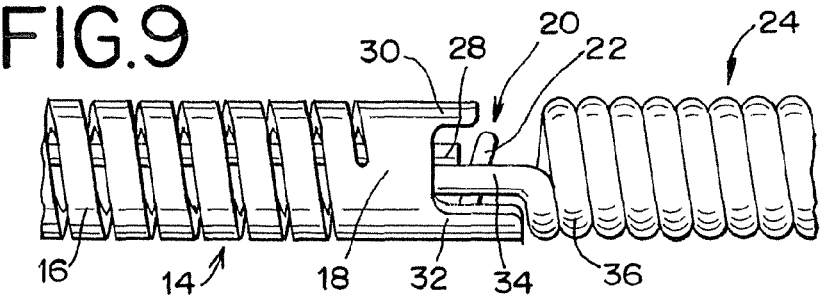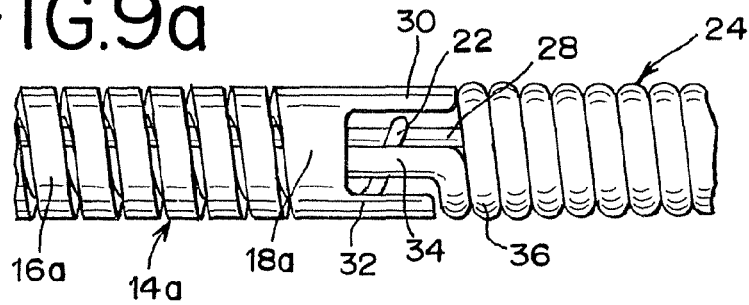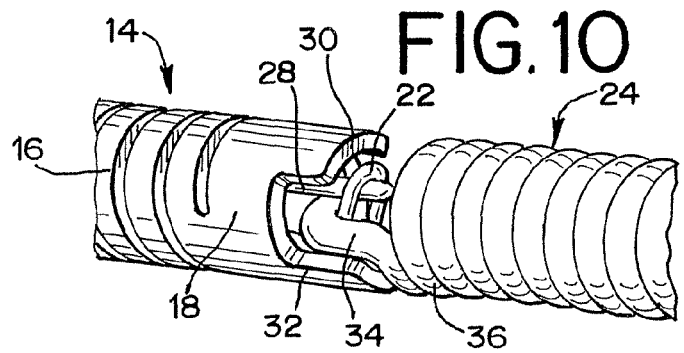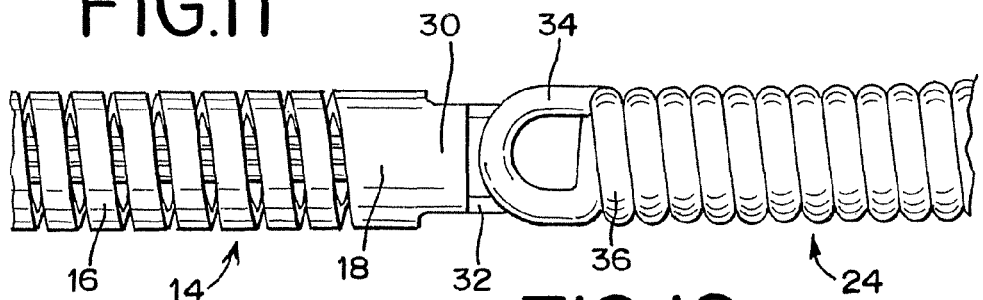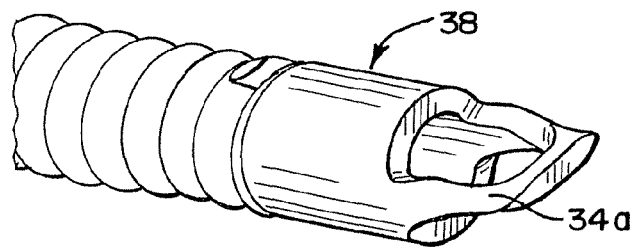

IMPLANTABLE MEDICAL DEVICE DETACHMENT SYSTEM AND METHODS OF USING THE SAME

FIELD OF THE INVENTION

This invention generally relates to interventional medical device systems that are navigable through body vessels of a human subject. More particularly, this invention relates to detachment systems for deploying an implantable medical device to a target location of a body vessel and methods of using the same.

DESCRIPTION OF RELATED ART

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat defects of the cranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the coil through the catheter and out of the distal end of the catheter into the delivery site. Some of the problems that have been associated with these procedures relate to ensuring the complete release and deployment of the coil. For example, U.S. Pat. No. 5,250,071 to Palermo, which is hereby incorporated herein by reference, describes a detachment system whereby interlocking clasps of the system and the coil are held together by a control wire. The control wire is moved proximally to disengage the clasps from each other. However, the system does not include any positive means for separating the disengaged clasps from each other, so merely retracting the control wire does not ensure release and deployment of the coil. Numerous other detachment systems currently in use suffer from similar problems.

Therefore, a need remains for a rapid release detachment system or method that can ensure release and deployment of an implantable medical device.

Further advantages could be realized with a detachment system or method incorporating a simple and inexpensive locking and deployment system.

SUMMARY OF THE INVENTION

In accordance with one embodiment or aspect of the present invention, a detachment system for delivering an implantable medical device to a target location of a body vessel is provided with a generally hollow tubular carrier member having a distal end and an engagement member associated with the distal end. The distal end includes a compressible portion that is axially adjustable between a compressed condition and an elongated condition. The engagement member is adapted to engage an implantable medical device when the compressible portion is in the compressed condition.

According to another embodiment or aspect of the present invention, a detachment system for delivering an implantable medical device to a target location of a body vessel is provided with a generally hollow tubular carrier member having a distal end and an engagement member associated with the distal end. The distal end includes a compressible portion that is axially movable from a compressed condition to an elongated condition. The engagement member is adapted to engage an implantable medical device when the compressible portion is in the compressed condition. Movement of the compressible portion to the elongated condition causes an implantable device engaged by the engagement member to be actively separated from the engagement member and deployed to the target location of the body vessel.

According to yet another embodiment or aspect of the present invention, a method of connecting an implantable medical device to a detachment system includes providing a generally hollow tubular carrier member. The carrier member has a distal end with a compressible portion that is axially movable from an elongated condition to a compressed condition. The compressible portion is moved to the compressed condition to expose at least a portion of an engagement member associated with the distal end. The exposed portion of the engagement member is then connected to an implantable medical device.

According to another embodiment or aspect of the present invention, a method of deploying an implantable medical device to a detachment system includes providing a generally hollow tubular carrier member. The carrier member has a distal end with a compressible portion in a compressed condition. An engagement member associated with the distal end is releasably connected to an implantable medical device. The thusly provided system is introduced into a body vessel and the implantable medical device is positioned generally adjacent to a target location of the vessel. When the implantable medical device is properly positioned, it is disengaged from the engagement member, which causes the compressible portion of the carrier member to axially elongate and actively deploy the implantable medical device.

Special application for the present invention has been found for deploying embolic coils to aneurysms in the neurovascular system. However, the present invention is also applicable to the deployment of other devices, including stents, to other portions of the vascular system, so it will be understood that the products and methods described herein are not limited to particular medical devices or particular surgical applications.

BRIEF DESCRIPTION OF THE DRAWINGS

FIG. 1 is a front elevational view of a carrier member of a detachment system according to an aspect of the present invention, in an elongated condition;

FIG. 1A is a bottom plan detail view of an anchor portion of the carrier member of FIG. 1;

FIG. 2 is a front perspective detail view of a distal end of the carrier member of FIG. 1;

FIG. 3 is a front elevational view of the carrier member of FIG. 1, in a compressed condition;

FIG. 4 is a front perspective detail view of a distal end of the carrier member of FIG. 3;

FIG. 9 is a front elevational view of a connection step for connecting the distal end and implantable medical device of FIG. 8;

FIG. 9a is a front elevational view of the proximal end of the pusher portion of FIG. 5 and illustrating a connection step by which the distal end of the pusher engages the proximal portion of the implantable medical device;

FIG. 10 is a front perspective detail view of the distal end of the carrier member and a rear perspective view of the implantable medical device of FIG. 8, in a connected condition;

FIG. 11 is a plan view of the distal end of the carrier member and proximal end of the implantable medical device of FIG. 8, in a disengaged condition; and FIG. 12 is a front perspective view of a head piece for an implantable medical device.

DESCRIPTION OF THE PREFERRED EMBODIMENTS

Figure 5:
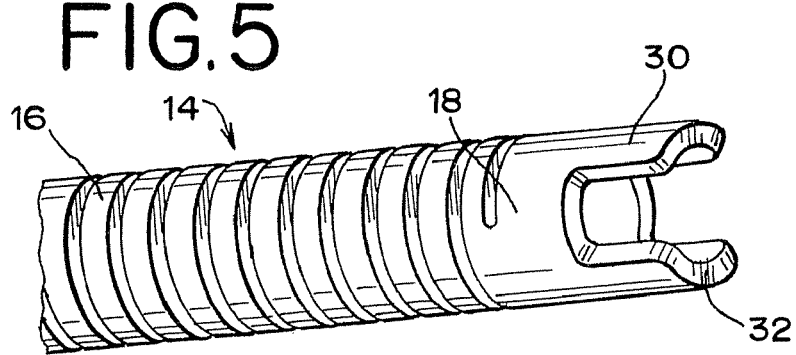
FIG. 5 is a front perspective view of a carrier member having a pusher portion according to an alternative embodiment.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIGS. 1-4 illustrate a distal portion of a generally hollow or tubular structure according to the present invention. When used herein, the terms "tubular" and "tube" are to be construed broadly and are not limited to a structure that is a right cylinder or strictly circumferential in cross-section or of a uniform cross-section throughout its length. For example, the tubular structure or system is generally designated at 10 and shown as a substantially right cylindrical structure. However, the tubular system may have a tapered or curved outer surface without departing from the scope of the present invention.

The detachment system 10 is comprised of a generally hollow tubular carrier member 12 having a distal end portion 14 with a compressible portion 16 and a pusher portion 18. Preferably, the carrier member 12 is a hypotube that may be comprised of a biocompatible material, such as stainless steel. The hypotube typically will have a diameter of between about 0.010 inch and about 0.015 inch, a preferred tube having a diameter of approximately 0.013 inch. Such a carrier member 12 is suitable for delivering and deploying embolic coils to target locations, typically aneurysms, within the neurovasculature, but differently sized carrier members comprised of other materials may be useful for different applications and are within the scope of the present invention.

The compressible portion 16 of the distal end portion 14 is axially adjustable between an elongated condition (FIGS. 1 and 2) and a compressed condition (FIGS. 3 and 4). Preferably, the compressible portion 16 comprises a spiral-cut portion of the carrier member 12, formed by a laser-cutting operation. However, any other arrangement allowing axial adjustment (e.g., a wound wire or spiral ribbon) is also suitable for use with detachment systems according to the present invention. Most preferably, the compressible portion 16 is in the elongated condition at rest and automatically or resiliently returns to the elongated condition from the compressed condition, unless otherwise constrained. The function of the compressible portion 16 will be described in greater detail herein.

When the compressible portion 16 is in the elongated condition, the distal end 14 receives and shields at least a portion of an engagement member 20, as shown in FIG. 2. The engagement member 20 is relatively small, having the thickness of a hair in some embodiments, so it may be preferred for it to be entirely shielded by the distal end 14 to prevent damage from accidental contact. In the embodiment of FIGS. 1-4, the engagement member 20 comprises an elongated wire loosely bent in half to define an opening 22. The ends 23 of the engagement member 20 are fixedly connected to the carrier member 12 at a position proximal to the compressible portion 16, for example at an anchor portion 26 (FIG. 1A).

Figure 6:
FIG. 6 is a plan view of an engagement member according to an alternative embodiment.
Figure 7:
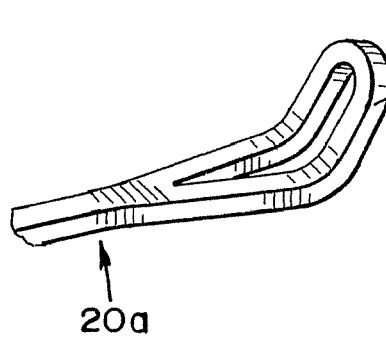
FIG. 7 is a front perspective detail view of the opening of the engagement member of FIG. 6, in an up-turned condition.
Figure 8:
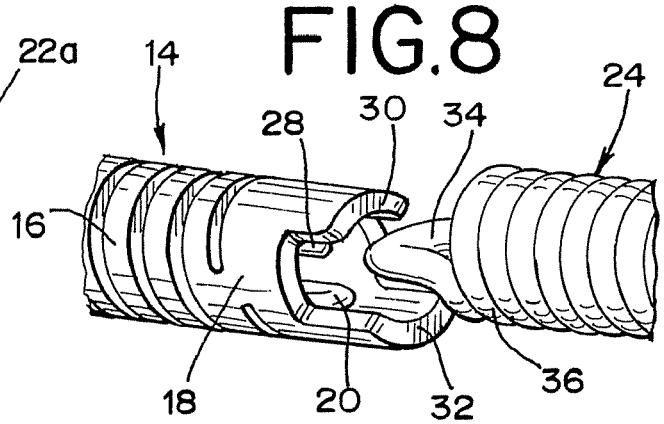
FIG. 8 is a front perspective view of the distal end of the carrier member of FIG. 1 and a rear perspective view of an implantable medical device in a pre-connection condition.

In an alternative embodiment, illustrated in FIGS. 6 and 7, the engagement member 20a comprises a flat ribbon defining an opening 22a at a distal portion thereof. FIG. 7 shows the opening 22a in an up-turned condition suitable for engaging an implantable medical device 24, as shown in FIGS. 9 and 10 and described in greater detail herein. The engagement member 20 of FIGS. 1-4 is preferably similarly deformable to the up-turned condition of FIGS. 9 and 10. Most preferably, the engagement member 20, 20a is elastically deformable to the up-turned condition of FIGS. 7, 9, and 10, such that it will return to the substantially flat condition of FIGS. 1-4 and 6 when not otherwise constrained. The engagement member 20, 20a may be comprised of any of a number of materials, including nitinol and stainless steel. The function of the engagement member 20, 20a will be described in greater detail herein.

As shown in FIGS. 1-4, the detachment system 10 further includes a locking member 26 received within the lumen of the carrier member 12 and movable with respect to the engagement member 20. The locking member 28 is preferably substantially longer than the engagement member 20, stretching beyond the anchor portion 26 to at least a proximal end portion (not illustrated) of the carrier member 12. In some embodiments, the locking member 28 stretches beyond a proximal end of the carrier member 12 to be directly manipulated by the user. The locking member 28 may be a wire comprised of any of a number of materials, including nitinol. The function of the locking member 28 will be described in greater detail herein.

The pusher portion 18 is positioned adjacent to and distally of the compressible portion 16. As shown in FIGS. 1-4, the pusher portion 18 preferably is not a simple right cylindrical member, but is a modified cylinder having a slot-like component, being defined by two arcuate extensions 30 and 32.

In one embodiment, the two extensions 30, 32 of the pusher portion 18 accommodate therebetween an aperture-defining proximal end portion 34 of an implantable medical device 24, which may be wider than the lumen of the carrier member 12, as shown in FIG. 11. Thus, the spacing that separates the two arcuate extensions 30 and 32 accommodates the proximal end member 34 and allows the engagement member 20 to engage the implantable medical device 24 (FIGS. 9 and 10), as described in greater detail herein. Furthermore, the engaged implantable medical device 24 may be rotated by rotating the carrier member 12 until at least one of the arcuate extensions 30, 32 bears against and turns the aperture-containing proximal end member 34 of the implantable medical device 24.

The arcuate extensions 30 and 32 of FIGS. 1-4 and 8-11 are illustrated with different lengths. As shown in FIG. 9, this creates a gap between the first arcuate extension 30 and a proximal end portion 36 of the implantable medical device 24, which may simplify connection of the device 24, as will be described in greater detail herein. However, according to an alternative embodiment of FIG. 5, the arcuate extensions 30 and 32 may have the same length without departing from the scope of the present invention. The function of the pusher portion 18 will be described in greater detail herein.

As for the implantable medical device 24, an embolic coil having a proximal end portion 36 with an aperture 34 is illustrated in FIGS. 8-11. However, it will be appreciated that virtually any implantable medical device may be delivered and deployed by detachment systems according to the present invention.

To connect the implantable medical device 24, the compressible portion 16 of the carrier member 12 is shortened in axial length to a compressed condition (FIGS. 3 and 4) to expose at least a portion of the engagement member 20. In particular, FIG. 3 shows a distance "D" by which the carrier member 12 is axially foreshortened in moving the compressible portion 16 from the elongated condition to the compressed condition. If the locking member 28 of the carrier member 12 is oriented to extend beyond the engagement member 20, as shown in FIGS. 3 and 4, it is withdrawn into the carrier member 12 sufficiently to position it clear of at least a portion of the opening 22 of the engagement member 20 (FIG. 9).

With the engagement member 20 exposed and clear of the locking member 28, the aperture-containing proximal end member 34 of the implantable medical device 24 is placed adjacent to opening 22, which is then deformed to the up-turned condition of FIG. 9. Alternatively, the opening 22 may be moved to the up-turned condition prior to placement of the implantable medical device 24. In the up-turned condition, at least a portion of the opening 22 passes through the aperture-containing portion 34, as best shown in FIG. 10. If the device is not provided with a suitable aperture, then a head piece 38 may be affixed to a proximal end portion thereof (FIG. 12) to provide an aperture 34a to receive the engagement member 20.

If the first arcuate extension 30 of the pusher portion 18 is relatively short compared to the second arcuate extension 32, then the second extension 32 will bear against the implantable medical device 24, while a gap is defined between the device 24 and the first arcuate extension 30, as illustrated in FIG. 9. The gap allows improved access to the engagement member 20, thereby simplifying movement thereof through the aperture 34 of the implantable medical device 24.

As described herein, the engagement member 20 is preferably elastically deformable to the up-turned condition of FIG. 9, so it will tend to return to a substantially flat condition. In order to prevent this, and to consequently lock the implantable medical device 24 to the engagement member 20, the locking member 28 is moved axially through the opening 22 to the position of FIG. 10. In this connected condition, the locking member 28 holds the engagement member 20 in the up-turned condition, and the engagement member 20 holds the proximal end portion 36 of the implantable medical device 24 against at least one arcuate extent 30, 32 of the pusher portion 18, preventing the compressible portion 16 from moving to the elongated condition.

Although an engagement system according to the preceding description is preferred for use with a detachment system of the present invention, other engagement systems may be used without departing from the present invention. For example, it is known to use heat-release adhesive to detach an implantable medical device from a delivery system. One such device is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. Such an engagement system may be incorporated into the present invention by orienting the engaged embolic coil to bear against the pusher portion 18 and hold the compressible portion 16 in the compressed condition while the adhesive is intact. Of course, the adhesive should be sufficiently strong to prevent release by the force of the compressible portion 16 acting on the embolic coil through the pusher portion 18.

Regardless of the engagement means employed to secure the implantable medical device 24, a device thus engaged is preferably delivered to a target location within a body vessel by a separate catheter or introducer. According to one method of delivering the device 24, a tubular catheter is fed into a body vessel until a distal end thereof is adjacent to a target location. Thereafter, the detachment system 10 and associated implantable medical device 24 are advanced through the catheter until the device 24 is itself generally adjacent to the target location. Alternatively, the detachment system 10 and associated device 24 may be pre-loaded in the catheter, with the combination being fed through a body vessel to a target location. Other methods of positioning the implantable medical device 24 generally adjacent to a target location may also be practiced without departing from the scope of the present invention.

To more accurately position the engaged device 24, radiopaque markers (not illustrated) may be attached to the carrier member 12 or the device 24 itself.

When the engaged device 24 has been properly positioned and oriented, it is disengaged from the engagement member 20. In the illustrated embodiment, this is achieved by moving the locking member 28 proximally from the position of FIG. 10 to the position of FIG. 9. In the position of FIG. 9, the engagement member 20 is allowed to return to its original substantially flat condition (FIGS. 3 and 4), thereby disengaging the aperture-containing end portion 34 of the implantable medical device 24. The locking member 28 may be provided with a radiopaque portion to provide visual feedback to indicate when the device 24 has been released.

One suitable method of withdrawing the locking member 28 is described in greater detail in an application entitled "Interventional Medical Device System Having an Elongation Retarding Portion and Method of Using the Same" Ser. No. 11/461,231, filed herewith on Jul. 31, 2006, which is hereby incorporated herein by reference. Briefly, the carrier member 28 may include a proximal portion with an elongatable portion defined by a series of alternating cut sections and frangible bridge members arranged in a spiral or helical pattern. A proximal end of the locking member 28 (not illustrated) is fixedly attached to the carrier member 12 at a location proximal to the elongatable portion. The elongatable portion is elongated by a user, thereby retracting the locking member 28. In one embodiment, the locking member 28 is adapted such that it will not disengage the engagement member 20 until a sufficient pull force is applied to break the frangible bridge members and more fully elongate the elongatable portion. Such an embodiment functions as a safety mechanism, because the implantable medical device 24 cannot be released until a minimum pull force is applied by the user.

When the implantable medical device 24 is disengaged from the engagement member 20, the compressible portion 16 automatically or resiliently moves from the compressed condition of FIG. 9 to the elongated condition of FIG. 11. At least one of the arcuate extensions 30, 32 of the pusher portion 18 bears against the device 24, completely separating it from the engagement member 20. Preferably, the pusher portion 18 bears against the proximal end portion 36 of the device 24 without contacting the aperture-containing proximal end portion 34, as illustrated in FIG. 10, because the proximal end portion 36 is typically sturdier than the aperture 34.

In the embodiment of FIG. 5 and FIG. 9a, the pusher portion 18a is designed to bear against one or more of the coils of the illustrated embolic device 24 when separating the aperture-containing end portion 34 of the device 24 from the engagement member 22. First arcuate extension 30 has a distal end surface that engages an upper edge (as viewed in FIG. 9a) of the distal-most turn of the device 24 (or a distal-most surface of a portion of some other device to be implanted). This engagement securely holds the device and protects the rest of the device, especially the extending portion 34, during disengagement. It also is contemplated that the second arcuate extension 32 has a distal end surface that engages a lower edge (as viewed in FIG. 9a) of the distal-most turn at this portion of the device 24 (or distal-most surface of some other device). This engagement securely holds this portion of the device during disengagement. By combining engagement between the device at locations that flank the aperture-containing proximal end portion 34 by the arcuate extensions 30, 32 respectively, an especially protective engagement is effected during pushing and disengaging action.

Ultimately, the force of the compressible portion 16 automatically or resiliently moving from the compressed condition to the elongated condition will force the implantable medical device 24 some distance from the engagement member 20, as shown in FIG. 11. The distance is exaggerated in FIG. 11 for illustrative purposes, as the compressible portion 16 is preferably calibrated such that its elongation will move the device 24 away from the engagement member 20 without expelling the same a significant distance from the pusher portion 18.

It will be seen from the preceding description that detachment systems according to the present invention eliminate numerous problems associated with known devices. In particular, detachment systems and associated methods of use according to the present invention ensure that the implantable device is completely separated from the engagement system and deployed to the target location.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A detachment system for delivering an implantable medical device to a target location of a body vessel, comprising:
   a generally hollow tubular carrier member having a distal end, wherein a compressible portion of said distal end is a spiral-cut portion of the carrier member itself and is axially adjustable between a compressed condition and an elongated condition;
   an engagement member associated with the distal end of the carrier member, wherein said engagement member has an up-turned condition at the distal end portion thereof, in which condition the engagement member has an up-turned distal end portion;
   a pusher portion of the carrier member positioned adjacent to and distally of the compressible portion, wherein said pusher portion is modified from a right cylindrical shape to accommodate a proximal end portion of the implantable medical device;
   an elongated locking member received within the carrier member and axially movable with respect to the engagement member and with respect to the tubular carrier member;
   said engagement member distal end portion thereof has an opening, and at least a portion of the elongated locking member is receivable by the up-turned engagement member opening, wherein an engagement space is defined by and partially bounded by said up-turned engagement member distal end portion and said locking member, which engagement space is adapted to engage an implantable medical device when the compressible portion of the tubular carrier member is in the compressed condition; and
   wherein the engagement member is substantially unexposed when said compressible portion of the distal end is in the elongated condition, and wherein at least a portion of the engagement member is exposed when said compressible portion is in the compressed condition.

2. The detachment system of claim 1, wherein the locking member releasably locks the up-turned engagement member and the engagement space releasably locks the implantable medical device.

3. The detachment system of claim 1, wherein said pusher portion includes a plurality of extensions that flank a proximally extending portion of the proximal end portion of the implantable medical device.

4. The detachment system of claim 3, wherein one of said flanking extensions is shorter than the other flanking extension.

5. The detachment system of claim 3, wherein at least one of said flanking extensions engages a proximal face of the implantable medical device.

6. The detachment system of claim 3, wherein at least two of said flanking extensions engage a respective proximal face portion of the implantable medical device.

7. A detachment system for delivering an implantable medical device to a target location of a body vessel, comprising:
   a generally hollow tubular carrier member having a distal end, wherein a compressible portion of said distal end is a spiral-cut portion of the carrier member itself and is axially movable from a compressed condition to an elongated condition;
   an engagement member associated with the distal end of the carrier member, wherein said engagement member has an up-turned condition at the distal end portion thereof, in which condition the engagement member has an up-turned distal end portion, wherein said compressible portion is adapted to deploy an implantable medical device engaged by the engagement member when said compressible portion moves to the elongated condition;
   a pusher portion of the carrier member positioned adjacent to and distally of the compressible portion, wherein said pusher portion is generally non-tubular to accommodate a proximal end portion of the implantable medical device;

an elongated locking member received within the carrier member and axially movable with respect to the engagement member and with respect to the tubular carrier member; and said engagement member distal end portion thereof has an opening, and at least a portion of the elongated locking member is receivable by the up-turned engagement member opening, wherein an engagement space is defined by and partially bounded by said up-turned engagement member distal end portion and said locking member, which engagement space is adapted to engage an implantable medical device when the compressible portion of the tubular carrier member is in the compressed condition; and wherein the engagement member is substantially unexposed when said compressible portion of the distal end is in the elongated condition, and wherein at least a portion of the engagement member is exposed when said compressible portion is in the compressed condition.

8. The detachment system of claim 7, wherein said compressible portion of the distal end of the carrier member is adapted to automatically/resiliently move to the elongated condition when the engagement member is disengaged from the implantable medical device.

9. The detachment system of claim 7, wherein said pusher portion comprises a first arcuate extension and a second arcuate extension, and wherein at least one of said first and second arcuate extensions is adapted to bear against the implantable medical device when the compressible portion of the distal end moves to the elongated condition.

10. The detachment system of claim 9, wherein one of said first and second arcuate extensions is longer than the other.

11. The detachment system of claim 9, wherein the first and second arcuate extensions have substantially the same length.

* * * * *